United States Patent [19]

Berg et al.

[11] Patent Number: 4,840,707

[45] Date of Patent: Jun. 20, 1989

[54] SEPARATION OF 3-METHYL-2-BUTANONE FROM FORMIC ACID BY EXTRACTIVE DISTILLATION

[75] Inventors: Lloyd Berg, 1314 S. Third Ave., Bozeman, Mont. 59715; Richard R. Rall, Bozeman, Mont.

[73] Assignee: Lloyd Berg, Bozeman, Mont.

[21] Appl. No.: 291,961

[22] Filed: Dec. 30, 1988

[51] Int. Cl.[4] .................. B01D 3/40; C07C 45/83; C07C 53/02
[52] U.S. Cl. ........................ 203/51; 203/56; 203/60; 203/61; 203/62; 203/63; 203/64; 562/609; 568/410
[58] Field of Search ............... 203/60, 51, 61, 62, 203/63, 64, 56; 568/410; 562/609

[56] References Cited

U.S. PATENT DOCUMENTS

| | | | |
|---|---|---|---|
| 2,010,384 | 8/1935 | vanMelsen et al. | 568/410 |
| 3,013,954 | 12/1961 | Pacoud et al. | 203/62 |
| 3,228,985 | 1/1966 | Carpenter et al. | 568/410 |
| 4,551,208 | 11/1985 | Bott et al. | 203/60 |
| 4,678,544 | 7/1987 | Wideman | 568/410 |
| 4,735,690 | 4/1988 | Berg et al. | 203/60 |
| 4,793,901 | 12/1988 | Berg et al. | 203/60 |

*Primary Examiner*—Wilbur Bascomb

[57] ABSTRACT

3-Methyl-2-butanone cannot be removed from 3-methyl-2-butanone and formic acid mixtures by distillation because of the presence of the maximum azeotrope between 3-methyl-2-butanone and formic acid. 3-Methyl-2-butanone can be readily removed from 3-methyl-2-butanone - formic acid mixtures by extractive distillation in which the extractive agent is dimethylacetamide, dimethylformamide or these with certain high boiling organic compounds.

4 Claims, No Drawings

SEPARATION OF 3-METHYL-2-BUTANONE FROM FORMIC ACID BY EXTRACTIVE DISTILLATION

FIELD OF THE INVENTION

This invention relates to a method for separating 3-methyl-2-butanone from formic acid using certain higher boiling liquids as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile component of the close boiling mixtures and the extractive agent are continuously removed from the column. The usual methods of separation of these two components are the use of another rectification column, cooling and phase separation or solvent extraction.

3-Methyl-2-butanone, B.P.=95.4° C. and formic acid, B.P.=100.8° C. form a maximum azeotrope boiling at 102.2° C. and containing 85 wt.% formic acid. When these two are found together in mixtures, either alone or with other liquids, distillation will only produce the azeotrope, never pure 3-methyl-2-butanone or formic acid. Thus any liquid mixture containing these two will upon distillation produce the azeotrope. Extractive distillation would be an attractive method of effecting the separation of 3-methyl-2-butanone from formic acid if agents can be found that (1) will break the 3-methyl-2-butanone - formic acid azeotrope and (2) are easy to recover from the formic acid, that is, form no azeotrope with formic acid and boil sufficiently above formic acid to make the separation by rectification possible with only a few theoretical plates.

Extractive distillation typically requires the addition of an equal amount to twice as much extractive agent as the formic acid - 3-methyl-2-butanone on each plate of the rectification column. The extractive agent should be heated to about the same temperature as the plate on to which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

Berg, U.S. Pat. No. 4,692,219 separated formic acid from acetic acid by extractive distillation. Extractive distillation was used by Berg, U.S. Pat. No. 4,735,690 to remove water and impurities from formic acid and Berg, U.S. Pat. No. 4,793,901 to break the 2-pentanone - formic acid azeotrope.

OBJECTIVE OF THE INVENTION

The object of this invention is to provide a process or method of extractive distillation that will enhance the relative volatility of 3-methyl-2-butanone from formic acid in their separation in a rectification column. It is a further object of this invention to identify suitable extractive distillation agents that will eliminate the 3-methyl-2-butanone - formic acid azeotrope and make possible the production of pure 3-methyl-2-butanone and formic acid by rectification. It is a further object of this invention to identify certain amides which in addition to the above constraints, are stable, can be separated from formic acid by rectification with relatively few theoretical plates and can be recycled to the extractive distillation column and reused with little or no decomposition.

SUMMARY OF THE INVENTION

The objects of the invention are provided by a process for separating 3-methyl-2-butanone from formic acid which entails the use of dimethylformamide or dimethylacetamide, either alone or admixed with certain oxygenated organic compounds as the agents in extractive distillation.

TABLE 1

Extractive Distillation Agents Which Are Effective In Breaking The 3-Methyl-2-butanone - Formic Acid Azeotrope

| Compounds | Ratios | | Relative Volatility | |
|---|---|---|---|---|
| Dimethylformamide (DMFA), Adipic acid | $(1/2)^2$ | $(3/5)^2$ | 4.9 | 3.1 |
| DMFA, Acetyl salicylic acid | " | " | 1.5 | 3.8 |
| DMFA, Benzoic acid | " | " | 2.2 | 2.4 |
| DMFA, Cinnamic acid | " | " | 3.0 | 3.3 |
| DMFA, Decanoic acid | " | " | 2.7 | 4.0 |
| DMFA, Heptanoic acid | " | " | 1.9 | 1.3 |
| DMFA, Neodecanoic acid | " | " | 1.7 | 1.6 |
| DMFA, Octanoic acid | " | " | 2.2 | 2.5 |
| DMFA, Pelargonic acid | " | " | 3.5 | 2.1 |
| DMFA, Adipic acid, Cyclohexanone | $(1/3)^3$ | $(2/5)^3$ | 3.5 | 2.5 |
| DMFA, Acetyl salicylic acid, Benzyl benzoate | " | " | 1.4 | 1.8 |
| DMFA, Benzoic acid, Isophorone | " | " | 1.6 | 2.5 |
| DMFA, Cinnamic acid, Butyl ether | " | " | 1.9 | 2.1 |
| DMFA, Decanoic acid, Butyl benzoate | " | " | 3.5 | 3.2 |
| DMFA, Heptanoic acid, Adiponitrile | " | " | 3.9 | 3.5 |
| DMFA, Neodecanoic acid, Ethyl benzoate | " | " | 2.2 | 3.3 |
| DMFA, Octanoic acid, Aceto- | " | " | 2.8 | 3.2 |

TABLE 1-continued

Extractive Distillation Agents Which Are Effective In Breaking The 3-Methyl-2-butanone - Formic Acid Azeotrope

| Compounds | Ratios | | Relative Volatility | |
|---|---|---|---|---|
| phenone | | | | |
| DMFA, Pelargonic acid, Methyl benzoate | " | " | 2.5 | 2.1 |
| Dimethylacetamide (DMAA) | 1 | 6/5 | 1.3 | 1.4 |
| DMAA, Adipic acid | $(1/2)^2$ | $(3/5)^2$ | 2.8 | 2.9 |
| DMAA, Acetyl salicylic acid | " | " | 2.7 | 2.6 |
| DMAA, Azelaic acid | " | " | 2.5 | 1.9 |
| DMAA, Benzoic acid | " | " | 2.7 | 1.4 |
| DMAA, 2-Benzoyl benzoic acid | " | " | 2.4 | 2.0 |
| DMAA, 4-tert. Butyl benzoic acid | " | " | 1.8 | 1.7 |
| DMAA, Decanoic acid | " | " | 2.6 | 3.0 |
| DMAA, Dodecanedioic acid | " | " | 2.7 | 1.7 |
| DMAA, Glutaric acid | " | " | 1.2 | 1.2 |
| DMAA, Heptanoic acid | " | " | 2.2 | 2.1 |
| DMAA, Hexanoic acid | " | " | 1.4 | 1.4 |
| DMAA, 4-Hydroxybenzoic acid | " | " | 1.1 | 1.1 |
| DMAA, Itaconic acid | " | " | 1.1 | 1.1 |
| DMAA, Malic acid | " | " | 1.2 | 1.2 |
| DMAA, Neodecanoic acid | " | " | 2.4 | 3.3 |
| DMAA, Neopentanoic acid | " | " | 1.2 | 1.6 |
| DMAA, Octanoic acid | " | " | 1.6 | 3.0 |
| DMAA, Pelargonic acid | " | " | 2.7 | 2.6 |
| DMAA, Salicylic acid | " | " | 1.0 | 1.2 |
| DMAA, Sebacic acid | " | " | 1.2 | 1.4 |
| DMAA, o-Toluic acid | " | " | 1.0 | 1.1 |
| DMAA, m-Toluic acid | " | " | 1.1 | 1.2 |
| DMAA, p-Toluic acid | " | " | 1.1 | 1.0 |
| DMAA, Adipic acid, 2-Octanone | $(1/3)^3$ | $(2/5)^3$ | 2.4 | 2.6 |
| DMAA, Acetyl salicylic acid, Isophorone | " | " | 5.0 | 3.4 |
| DMAA, Azelaic acid, Benzyl benzoate | " | " | 1.8 | 1.4 |
| DMAA, Benzoic acid, Benzyl ether | " | " | 1.4 | 1.8 |
| DMAA, 2-Benzoyl benzoic acid, Ethylene glycol butyl ether acetate | " | " | 2.1 | 3.3 |
| DMAA, 4-tert. Butyl benzoic acid, Butyl ether | " | " | 3.5 | 3.5 |
| DMAA, Glutaric acid, Methyl salicylate | " | " | 1.1 | 1.1 |
| DMAA, Heptanoic acid, Methyl benzoate | " | " | 2.0 | 2.5 |
| DMAA, Hexanoic acid, Methyl salicylate | " | " | 2.1 | 2.1 |
| DMAA, 4-Hydroxybenzoic acid, Dipropylene glycol dimethyl ether | " | " | 1.2 | 1.1 |
| DMAA, Itaconic acid, Isobutyl heptyl ketone | " | " | 1.1 | 1.1 |
| DMAA, Malic acid, Ethylene glycol methyl ether acetate | " | " | 1.1 | 1.1 |
| DMAA, Neodecanoic acid, Cyclohexanone | " | " | 1.1 | 1.0 |
| DMAA, Neopentanoic acid, Ethylene glycol methyl ether acetate | " | " | 2.2 | 2.3 |
| DMAA, Octanoic acid, Ethyl benzoate | " | " | 2.1 | 3.9 |
| DMAA, Pelargonic acid, Butyl benzoate | " | " | 1.6 | 2.8 |
| DMAA, Sebacic acid, Propylene glycol dimethyl ether | " | " | 1.1 | 1.1 |
| DMAA, o-Toluic acid, Hexyl acetate | " | " | 1.2 | 1.1 |
| DMAA, m-Toluic acid, Hexyl acetate | " | " | 1.1 | 1.1 |
| DMAA, p-Toluic acid | " | " | 1.2 | 1.1 |

TABLE 2

Potential Extractive Distillation Agents Which Were Ineffective - Decomposed The Formic Acid Dimethylformamide (DMFA)
DMFA, Azelaic acid
DMFA, p-tert. Butyl benzoic acid
DMFA, Glutaric acid
DMFA, Itaconic acid
DMFA, Hexanoic acid
DMFA, Salicylic acid
DMFA, Sebacic acid
DMFA, o-Toluic acid
DMFA, Azelaic acid, Benzyl ether
DMFA, Glutaric acid, Diethylene glycol diethyl ether
Dimethylacetamide (DMAA), Cinnamic acid
DMAA, Cinnamic acid, Diethylene glycol diethyl ether

TABLE 3

Data From Runs Made In Rectification Column

| Agent | Column | Time Hrs. | Weight % 3-Me—2-butan. | Weight % Formic acid | Relative Volatility |
|---|---|---|---|---|---|
| 33% Dimethylformamide 33% Heptanoic acid 33% Methyl benzoate | Overhead Bottoms | 3/4 | 90.4 17.4 | 9.6 82.6 | 2.28 |
| 33% Dimethylformamide 33% Heptanoic acid 33% Methyl benzoate | Overhead Bottoms | 1.5 | 90.7 15.4 | 9.3 84.6 | 2.37 |
| Dimethylacetamide | Overhead Bottoms | 3/4 | 90.1 42.1 | 9.9 57.9 | 1.52 |
| Dimethylacetamide | Overhead Bottoms | 1.5 | 93.8 23.1 | 6.2 76.9 | 2.42 |

DETAILED DESCRIPTION OF THE INVENTION

We have discovered that dimethylformamide and dimethylacetamide, either alone or admixed with other organic compounds, will effectively negate the 3-methyl-2-butanone azeotrope and permit the separation of pure 3-methyl-2-butanone from formic acid by rectification when employed as the agent in extractive distillation. Table 1 lists dimethylformamide, dimethylacetamide and their mixtures in the proportions that we have found to be effective. The data in Table 1 was obtained in a vapor-liquid equilibrium still. In each case, the starting material was the 3-methyl-2-butanone —formic acid azeotrope. The ratios are the parts by weight of extractive agent used per part of 3-methyl-2-butanone—formic acid azeotrope. The relative volatilities are listed for each of the two ratios employed. The compounds which are effective when used in mixtures with dimethylformamide or dimethylacetamide are adipic acid, acetyl salicylic acid, benzoic acid, cinnamic acid, decanoic acid, heptanoic acid, neodecanoic acid, octanoic acid, pelargonic acid, cyclohexanone, benzyl benzoate, isophorone, butyl ether, butyl benzoate, adiponitrile, ethyl benzoate, acetophenone, methyl benzoate, azelaic acid, 2-benzoyl benzoic acid, 4-tert. butyl benzoic acid, dodecanedioic acid, glutaric acid, hexanoic acid, 4-hydroxybenzoic acid, itaconic acid, malic acid, neopentanoic acid, salicylic acid, sebacic acid, o-toluic acid, m-toluic acid, p-toluic acid, 2-octanone, benzyl benzoate, benzyl ether, ethylene glycol butyl ether acetate, methyl salicylate, dipropylene glycol dimethyl ether, isobutyl heptyl ketone, ethylene glycol methyl ether acetate, ethylene glycol methyl ether acetate, propylene glycol dimethyl ether and hexyl acetate. The two relative volatilities shown in Table 1 correspond to the two different ratios invetsigated. For example, in Table 1, one-half part of dimethylformamide plus one-half part of benzoic acid with one part of the 3-methyl-2-butanone—formic acid azeotrope gives a relative volatility of 2.2; 3/5 parts of DMFA plus 3/5 parts of benzoic acid give 2.4. One third parts each dimethylacetamide, benzoic acid and benzyl ether with one part of the 3-methyl-2-butanone—formic acid azeotrope gives a relative volatility of 1.4, with two-fifths parts, these three give 1.8. In every example in Table 1, the starting material is the 3-methyl-2-butanone—formic acid azeotrope which possesses a relative volatility of 1.00.

Table 2 shows twelve mixtures containing dimethylformamide or dimethylacetamide which might be expected to be effective extractive distillation agents for this separation but which were not. The principal difficulty encountered with these agents was that they decompose the formic acid when boiled with it in the still.

Two of the agents, dimethylformamide plus heptanoic acid plus methyl benzoate, and dimethylacetamide, listed in TAble 1 and whose relative volatility had been determined in the vapor liquid equilibrium still, were then evaluated in a glass perforated plate rectification column possessing 5.3 theoretical plates and the results listed in Table 3. The data in Table 3 was obtained in the following manner. The charge was 200 grams of the formic acid—3-methyl-2-butanone azeotrope and after half an hour of operation in the 5.3 theoretical plate column to establish equilibrium, DMFA, heptanoic acid and methyl benzoate at 95° C. and 20 ml/min. was pumped in. The rectification was continued with the first sampling of the overhead and bottoms after ¾ hours. The analyses are shown in Table 3 and were overhead 90.4% 3-Me-2-butanone, 9.6% formic acid and the bottoms was 17.4% 3-Me-2-butanone, 82.6% formic acid which gives a relative volatility of 3-Me-2-butanone to formic acid of 2.28. This indicates that the azeotrope has been negated and separation accomplished. Without the extractive agent, the overhead would have been the azeotrope composition. This proves that the extractive agent is negating the azeotrope and makes the rectification proceed as if the azeotrope no longer existed thus bringing out the more volatile 3-Me-2-butanone as overhead.

THE USEFULNESS OF THE INVENTION

The usefulness or utility of this invention can be demonstrated by referring to the data presented in Tables 1 and 3. All of the successful extractive distillation agents show that 3-methyl-2-butanone and formic acid can be separated from their maximum azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity 3-methyl-2-butanone and formic acid from any mixture of these two including the maximum azeotrope. The stability of the compounds used and the boiling point difference is such that complete recovery and recycle is obtainable by a simple distillation and the amount required for make-up is small.

WORKING EXAMPLES

Example 1

Fifty grams of the 3-methyl-2-butanone—formic acid azeotrope and 50 grams of dimethylacetamide (DMAA) were charged to a vapor-liquid equilibrium still and refluxed for 12 hours. Analysis by gas chromaography indicated a vapor composition of 33.3% 3-methyl-2-butanone, 66.7% formic acid, a liquid composition of 28.2% 3-methyl-2-butanone, 71.8% formic acid which is a relative volatility of 1.3. Ten grams of DMAA were added and refluxing continued for another eight hours. Analysis indicated a vapor composition of 43.5% 3-methyl-2-butanone, 56.5% formic acid, a liquid composition of 35.1% 3-methyl-2-butanone, 64.9% formic acid which is a relative volatility of 1.4.

Example 2

Fifty grams of the 3-methyl-2-butanone—formic acid azeotrope, 25 grams of dimethylacetamide (DMAA) and 25 grams of pelargonic acid were charged to the vapor-liquid equilibrium still and refluxed for 18 hours. Analysis indicated a vapor composition of 55.9% 3-methyl-2-butanone, 44.1% formic acid and a liquid composition of 31.8% 3-methyl-2-butanone, 68.2% formic acid which is a relative volatility of 2.7. Five grams of DMAA and five grams of pelargonic acid were added and refluxing continued for another eight hours. Analysis indicated a vapor composition of 48.9% 3-methyl-2-butanone, 51.1% formic acid and a liquid composition of 26.7% 3-methyl-2-butanone, 73.3% formic acid which is a relative volatility of 2.6.

Example 3

Fifty grams of the 3-methyl-2-butanone—formic acid azeotrope, 25 grams of dimethylformamide (DMFA) and 25 grams of pelargonic acid were charged to the vapor-liquid equilibrium still and refluxed for 12 hours. Analysis indicated a vapor composition of 19.8% 3-methyl-2-butanone, 80.2% formic acid and a liquid composition of 6.5% 3-methyl-2-butanone, 93.5% formic acid which is a relative volatility of 3.5. Five grams each of DMFA and pelargonic acid were added and refluxing continued for another seven hours. Analysis indicated a vapor composition of 20.9% 3-methyl-2-butanone, 79.1% formic acid and a liquid composition of 11.1% 3-methyl-2-butanone, 88.9% formic acid which is a relative volatility of 2.1.

Example 4

A glass perforated plate rectification column was calibrated with methyl cyclohexane and toluene which possesses a relative volatility of 1.46 and found to have 5.3 theoretical plates. A solution comprising 200 grams of the 3-methyl-2-butanone—formic acid azeotrope was placed in the stillpot and heated. When refluxing began, an extractive agent comprising 33% dimethylformamide, 33% heptanoic acid and 33% methyl benzoate was pumped into the column at a rate of 20 ml/min. The temperature of the extractive agent as it entered the column was 95° C. After establishing the feed rate of the extractive agent, the heat input to the 3-methyl-2-butanone and formic acid in the stillpot was adjusted to give a total reflux rate of 50 ml/min. After ¾ hours of operation, the overhead and bottoms samples of approximately two ml. were collected and analyses by gas chromatography. The overhead analysis was 90.4% 3-methyl-2-butanone, 9.6% formic acid. The bottoms analysis was 17.4% 3-methyl-2-butanone, 82.6% formic acid. Using these compositions in the Fenske equation, with the number of theoretical plates in the column being 5.3, gave an average relative volatility of 2.28 for each theoretical plate. After 1.5 hours of continuous operation, the overhead analysis was 90.7% 3-methyl-2-butanone, 9.3% formic acid, the bottoms analysis was 15.4% 3-methyl-2-butanone, 84.6% formic acid which is a relative volatility of 2.37.

Example 5

Using the same column and conditions as in Example 4, an extractive agent comprising dimethylacetamide was employed. After ¾ hours of continuous operation, the overhead analysis was 90.1% 3-methyl-2-butanone, 9.9% formic acid and the bottoms analysis was 42.1% 3-methyl-2-butanone, 57.9% formic acid which is a relative volatility of 1.52. After 1.5 hours of continuous operation, the overhead analysis was 93.8% 3-methyl-2-butanone, 6.2% formic acid, the bottoms analysis was 23.1% 3-methyl-2-butanone, 76.9% formic acid which is a relative volatility of 2.42.

We claim:

1. A method for recovering 3-methyl-2-butanone from mixtures of 3-methyl-2-butanone and formic acid which comprises distilling a mixture of 3-methyl-2-butanone and formic acid in a rectification column in the presence of about one part of an extractive agent per part of the 3-methyl-2-butanone—formic acid mixture, recovering 3-methyl-2-butanone as overhead product and obtaining the extractive agent and the formic acid from the stillpot, wherein said extractive agent comprises a dimethyl amide containing three or four carbon atoms.

2. The method of claim 1 in which the extractive agent comprises dimethylacetamide.

3. The method of claim 1 in which the extractive agent comprises dimethylacetamide and at least one material selected from the group consisting of adipic acid, acetyl salicylic acid, azelaic acid, benzoic acid, 2-benzoyl benzoic acid, 4-tertiary butyl benzoic acid, decanoic acid, dodecanedioic acid, glutaric acid, heptanoic acid, hexanoic acid, 4-hydroxybenzoic acid, itaconic acid, malic acid, neodecanoic acid, neopentanoic acid, octanoic acid, pelargonic acid, salicylic acid, sebacic acid, o-toluic acid, m-toluic acid, p-toluic acid, 2-octanone, isophorone, benzyl benzoate, benzyl ether, ethylene glycol butyl ether acetate, butyl ether, methyl salicylate, methyl benzoate, cyclohexanone, dipropylene glycol dimethyl ether, isobutyl heptyl ketone, ethylene glycol methyl ether acetate, ethyl benzoate, butyl benzoate, hexyl acetate and propylene glycol dimethyl ether.

4. The method of claim 1 in which the extractive agent comprises dimethylformamide and at least one material selected from the group consisting of adipic acid, acetyl salicylic acid, benzoic acid, cinnamic acid, decanoic acid, heptanoic acid, neodecanoic acid, octanoic acid, pelargonic acid, cyclohexanone, benzyl benzoate, isophorone, butyl ether, butyl benzoate, adiponitrile, ethyl benzoate, acetophenone and methyl benzoate.

* * * * *